US009345723B2

(12) United States Patent
Mekhail et al.

(10) Patent No.: US 9,345,723 B2
(45) Date of Patent: May 24, 2016

(54) RAPID FORMATION OF CHITOSAN SPONGES USING GUANOSINE 5'-DIPHOSPHATE: INJECTABLE SCAFFOLDS FOR TISSUE REGENERATION AND DRUG DELIVERY

(71) Applicant: THE ROYAL INSTITUTION FOR THE ADVANCEMENT OF LEARNING/MCGILL UNIVERSITY, Montréal (CA)

(72) Inventors: Mina Mekhail, Montréal (CA); Guillermina Almazan, Montréal (CA); Maryam Tabrizian, Montréal (CA)

(*) Notice: Subject to any disclaimer, the term of this patent is extended or adjusted under 35 U.S.C. 154(b) by 0 days.

(21) Appl. No.: 14/424,643

(22) PCT Filed: Sep. 4, 2013

(86) PCT No.: PCT/CA2013/050677
§ 371 (c)(1),
(2) Date: Feb. 27, 2015

(87) PCT Pub. No.: WO2014/036649
PCT Pub. Date: Mar. 13, 2014

(65) Prior Publication Data
US 2015/0258132 A1  Sep. 17, 2015

Related U.S. Application Data

(60) Provisional application No. 61/696,537, filed on Sep. 4, 2012.

(51) Int. Cl.
*A61F 2/02* (2006.01)
*A61K 31/722* (2006.01)
(Continued)

(52) U.S. Cl.
CPC ............ *A61K 31/722* (2013.01); *A61K 9/0024* (2013.01); *A61K 9/1652* (2013.01); *A61K 31/713* (2013.01); *A61K 38/02* (2013.01); *A61K 38/18* (2013.01); *A61K 48/00* (2013.01); *A61L 27/20* (2013.01); *A61L 27/52* (2013.01); *A61L 27/54* (2013.01); *C08B 37/003* (2013.01); *C08K 5/529* (2013.01); *C08L 5/08* (2013.01); *A61K 47/26* (2013.01); *A61K 47/36* (2013.01); *A61L 2300/258* (2013.01); *A61L 2300/414* (2013.01); *A61L 2300/416* (2013.01); *A61L 2300/602* (2013.01); *A61L 2400/06* (2013.01); *A61L 2430/02* (2013.01); *A61L 2430/06* (2013.01); *A61L 2430/20* (2013.01);
(Continued)

(58) Field of Classification Search
CPC .... A61K 9/0024; A61K 9/1652; A61K 47/36
See application file for complete search history.

(56) References Cited

PUBLICATIONS

Woerly, "Spinal cord repair with PHPMA hydrogel containing RGD peptides (NeuroGel™)" Biomaterials, vol. 22, Issue 10, May 2001, pp. 1095-1111.
(Continued)

*Primary Examiner* — Carolos Azpuru
(74) *Attorney, Agent, or Firm* — Norton Rose Fulbright Canada LLP

(57) ABSTRACT

It is disclosed Guanosine 5'-Diphosphate (GDP) crosslinked chitosan sponge or gelling composition which is used as a scaffold for tissue regeneration applications such as neural, cardiac, cartilage and bone regeneration. In addition, the sponge acts as a drug delivery system to provide local controlled drug release, such as delivering anti-cancer drugs locally at the tumor site.

12 Claims, 5 Drawing Sheets

(51) Int. Cl.
*A61K 9/16* (2006.01)
*A61L 27/20* (2006.01)
*A61L 27/52* (2006.01)
*C08K 5/529* (2006.01)
*C08L 5/08* (2006.01)
*A61L 27/54* (2006.01)
*A61K 9/00* (2006.01)
*C08B 37/08* (2006.01)
*A61K 31/713* (2006.01)
*A61K 38/02* (2006.01)
*A61K 38/18* (2006.01)
*A61K 48/00* (2006.01)
*A61K 47/26* (2006.01)
*A61K 47/36* (2006.01)

(52) U.S. Cl.
CPC ......... *A61L 2430/24* (2013.01); *A61L 2430/30* (2013.01); *A61L 2430/32* (2013.01); *A61L 2430/34* (2013.01)

(56) References Cited

PUBLICATIONS

Crompton, "Morphology and gelation of thermosensitive chitosan hydrogels", Biophysical Chemistry, vol. 117, Issue 1, Aug. 22, 2005, pp. 47-53.

Bhattarai, "PEG-grafted chitosan as an injectable thermosensitive hydrogel for sustained protein release", Journal of Controlled Release, vol. 103, Issue 3, Apr. 18, 2005, pp. 609-624.

International search report and written opinion of corresponding PCT/CA2013/050677.

RAPID FORMATION OF CHITOSAN SPONGES USING GUANOSINE 5'-DIPHOSPHATE: INJECTABLE SCAFFOLDS FOR TISSUE REGENERATION AND DRUG DELIVERY

CROSS REFERENCE TO RELATED APPLICATION

This application claims priority from U.S. Provisional Application Ser. No. 61/696,537, filed Sep. 4, 2012, the entire content of which is incorporated herein by reference.

TECHNICAL FIELD

The present disclosure relates to Guanosine 5'-Diphosphate (GDP) crosslinked chitosan sponges.

BACKGROUND ART

Chitosan has been emerging as a promising biomaterial for a multitude of tissue regeneration and drug delivery applications (Prabaharan, 2008, Journal of Biomaterials Applications, 23: 5; Seo et al., 2008, Biotechnol Adv, 26: 1). The extensive research on chitosan has led to the development of many fabrication methods for the preparation of microparticles, nanoparticles, films, sponges, nanofibers, microfibers, and hydrogels (Panoe et al., 2008, Curr Drug Discov Technol, 5: 333; Bhattarai et al., 2010, Adv Drug Deliver Rev, 62: 83). This ability to fabricate chitosan using different methods makes it one of the most versatile naturally-derived biomaterials currently used. Chitosan sponges, specifically, are promising scaffolds for bone and cartilage tissue regeneration (Silva et al., 2008, Biomacromolecules, 9: 2765; Park et al., 2000, Biomaterials, 21: 153), and for a wide range of drug delivery applications (Arpornmaeklong et al., 2008, Int J Oral Max Surg, 37: 357; Pereira et al., 2005. Curr Drug Discov Technol, 2: 231; Ding et al., 2008, Process Biochem, 43: 287). Implantation of these sponges in situ is usually done via an invasive surgical procedure that requires recovery time and potential for infection during the wound healing process (Chesnutt et al., 2009, Tissue engineering. Part A, 15: 2571). Therefore, a minimally invasive procedure to form chitosan scaffolds in situ is desirable.

Injectable chitosan hydrogels have been widely explored in the literature, and stimuli, such as temperature, pH and UV-irradiation, have been used to trigger gelation in situ (Vaghani et al., 2012, Carbohyd Res, 347: 76; Tsuda et al., 2009, Artif Organs, 33:74). However, a fast rate of gelation, a key requirement, still remains less than ideal. A fast rate of gelation is desirable to keep the hydrogel localized at the site of injection. Thermosensitive Chitosan/β-Glycerophosphate hydrogels, extensively studied in the literature, were shown to gel in 4-9 minutes at 37° C. (Crompton et al., 2005, Biophys Chem, 117: 47). Another example is PEG-grafted chitosan that was shown to undergo a sol-gel transition in 10±4 minutes (Bhattarai et al., 2005, Journal of Controlled Release, 103: 609).

There is thus still a need to be provided with chitosan scaffolds or hydrogels with improved gelation properties.

SUMMARY

In accordance with the present description, there is now provided a gelling composition comprising chitosan and Guanosine 5'-Diphosphate (GDP), wherein the composition forms a gel when the chitosan is mixed with the GDP at a pH range from 5 to 6.

In another embodiment, it is provided a method of manufacturing a gelling composition comprising dissolving chitosan in an acidic medium, increasing the pH of chitosan between 5 and 6; and adding a solution containing Guanosine 5'-Diphosphate (GDP) forming a gel.

It is also provided a kit comprising a chitosan solution at a pH between 5 and 6, and a Guanosine 5'-Diphosphate (GDP) solution, wherein a gel is formed when the chitosan solution is mixed with the GDP solution.

In an embodiment, the composition gels in 1 to 5 seconds, preferably the composition gels in 1.6 seconds.

In another embodiment, the composition further comprises sodium bicarbonate.

In an embodiment, the composition comprises 1M of sodium bicarbonate.

In an embodiment, the composition comprises chitosan at a concentration of 3 mg/ml to 6 mg/ml.

In a supplemental embodiment, the chitosan has a degree of deacetylation of more than 85%, or a degree of deacetylation of more than 90%.

In an embodiment, the composition is for use in tissue regeneration of soft human tissues, cardiac regeneration, or cartilage regeneration.

In an embodiment, the composition is for use in neural regeneration.

In an embodiment, the composition is for use in bone regeneration.

In an embodiment, the soft human tissues are articular cartilage, spinal cord, brain, heart muscle or any cavity in contact with mucous, soft and/or hard tissue.

In an embodiment, the composition further comprises a therapeutic drug or a small molecule to be release in the site of interest.

In another embodiment, the drug is an anti-cancer drug.

In a further embodiment, the small molecule is an RNA-inducing nucleic acid molecule, such as for example a short interfering RNA, a short hairpin RNA or a RNAi-inducing vector.

Preferably, it is encompassed that the composition controls the anti-cancer drug release at a tumor site.

In an embodiment, the composition described herein can be used as a delivery vehicle for another drug or compound.

In an embodiment, the chitosan and GDP are formulated for injection, such as a separate injection, for example for a simultaneous injection.

In another embodiment, in the method described herein, the acidic medium is HCl.

In another embodiment, the pH of chitosan is increased by adding a sodium bicarbonate solution.

In an embodiment, the GDP solution and the chitosan solution are maintained at 37° C. separately before the solution of GDP is added to the chitosan solution.

In another embodiment, the chitosan solution and the GDP solution are manufactured in a double-barrel syringe or separate syringes.

It is also provided the use of the composition described herein for stimulating tissue regeneration of soft human tissues, cardiac regeneration, or cartilage regeneration.

It is also provided the use of the composition described herein for stimulating neural regeneration.

It is also provided the use of the composition described herein for stimulating bone regeneration.

It is also provided the use of the composition described herein in the manufacture of a medicament for stimulating tissue regeneration of soft human tissues, cardiac regeneration, or cartilage regeneration.

It is also provided the use of the composition described herein in the manufacture of a medicament for stimulating neural regeneration.

It is also provided the use of the composition described herein in the manufacture of a medicament for stimulating bone regeneration.

It is also provided the use of the composition described herein for delivering a drug or a compound in a patient.

It is also provided a method for stimulating tissue regeneration of soft human tissues, cardiac regeneration, or cartilage regeneration comprising administering to a patient the composition described herein.

It is also provided a method for stimulating neural regeneration comprising administering to a patient the composition described herein.

It is also provided a method for stimulating bone regeneration comprising administering to a patient the composition described herein.

It is further provided a method for delivering a drug or a compound in a patient, comprising administering to a patient the composition described herein.

BRIEF DESCRIPTION OF THE DRAWINGS

Reference will now be made to the accompanying drawings, showing by way of illustration:

FIGS. 1A, 1B, 1C and 1D are scanning electron microscopy (SEM) images of C3PH5, C3PH6, C6PH5 and C6PH6 respectively; FIG. 1E represents the water retention of the different four groups; FIG. 1F represents the gelation time (seconds); FIG. 1H demonstrates the Fourier transform infrared spectroscopy (FTIR) spectra of C6PH5, which was similar to the other sponges, as compared to GDP and chitosan powder; FIG. 1I represents the X-ray diffraction (XRD) spectra of the four sponges and a table of their crystallinity indices.

FIG. 3A: light microscopy images of 3T3 fibroblasts with different concentrations of GDP and TPP added to the culture media after 24 hours; FIG. 3B: Quantitative analysis, using MTT assay, of the cytotoxicity of TPP and GDP to 3T3 fibroblasts at different concentrations after 24 hours.

DETAILED DESCRIPTION

Figure 1:
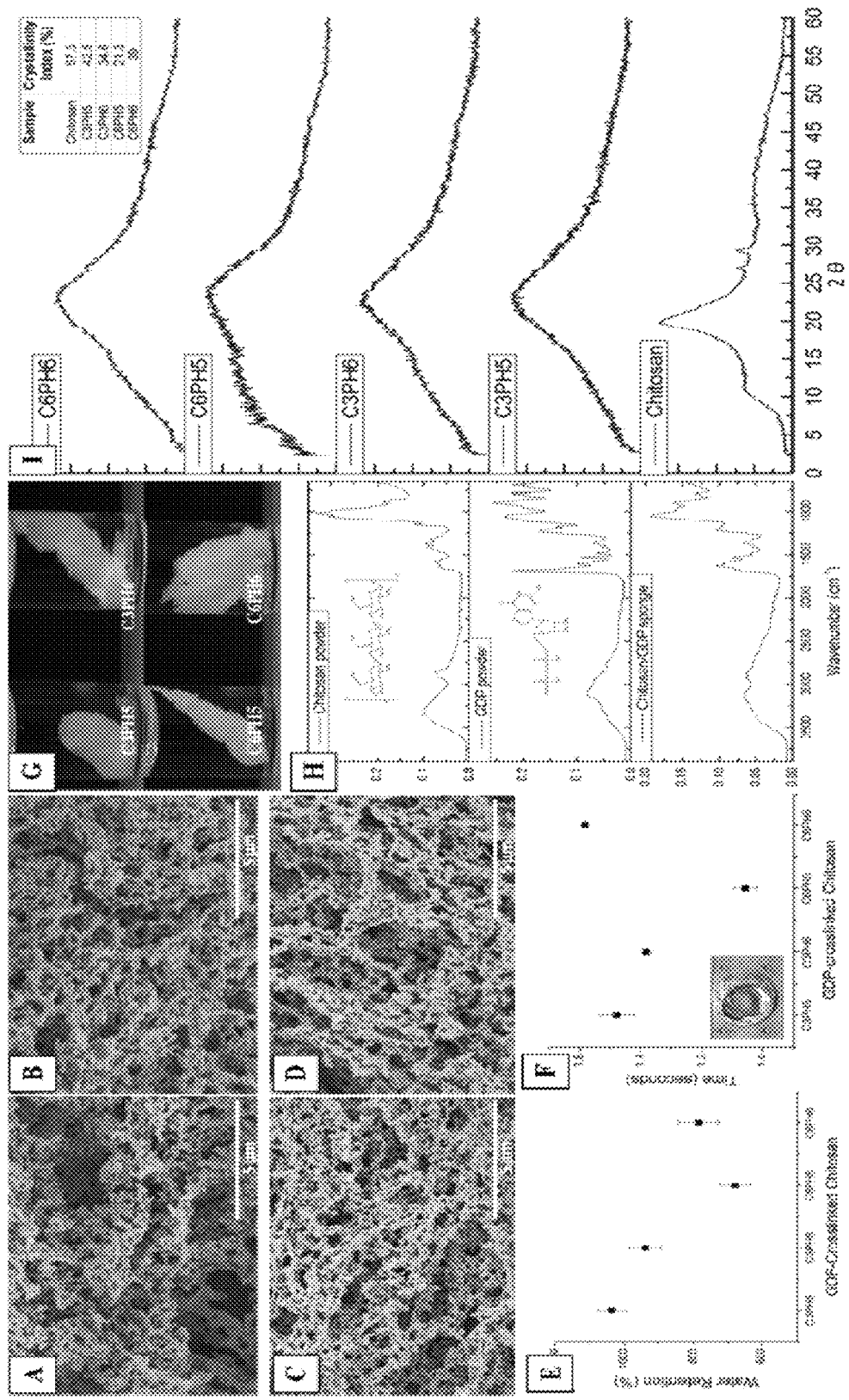
FIG. 1 illustrates the characterization of the GDP-crosslinked injectable chitosan sponges.

It is provided a gelling composition comprising chitosan and Guanosine 5'-Diphosphate (GDP), wherein the composition forms a gel when the chitosan is mixed with the GDP at a pH range from 5 to 6.

In comparison to current systems known in the art, the proposed Guanosine 5'-Diphosphate (GDP) crosslinked chitosan gel or sponge is superior since it undergoes gelation in less than 1.6 seconds as measured by an impedance analyzer. This fast gelation rate assures that the sponge formation is localized at the site of injection. The disclosed gel or sponge could be injected with know techniques and devices, such as the Twin-Syringe Biomaterial Delivery System (M-System™).

Chitosan is an amino polysaccharide obtained by partial to substantial alkaline N-deacetylation of chitin also named poly(N-acetyl-D-glucosamine), which is a naturally occurring biopolymer found in exoskeleton of crustaceans, such as shrimp, crab and lobster shells. Chitosan contains free amine (—$NH_2$) groups and may be characterized by the proportion of N-acetyl-D-glucosamine units and D-glucosamine units, which is expressed as the degree of deacetylation (DDA) of the fully acetylated polymer chitin. The properties of chitosan, such as the solubility and the viscosity, are influenced by the degree of deacetylation (DDA), which represents the percentage of deacetylated monomers, and the molecular weight (Mw).

Chitosan has been proposed in various formulations, alone and with other components, to stimulate repair of dermal, corneal and hard tissues in a number of reports (U.S. Pat. Nos. 4,572,906; 4,956,350; 5,894,070; 5,902,798; 6,124,273; and WO 98/22114). One technical difficulty that chitosan often presents is a low solubility at physiological pH and ionic strength, thereby limiting its use in a solution state. Thus typically, dissolution of chitosan is achieved via the protonation of amine groups in acidic aqueous solutions having a pH ranging from 3.0 to 5.6. Such chitosan solutions remain soluble up to a pH near 6.2 where neutralisation of the amine groups reduces interchain electrostatic repulsion and allows attractive forces of hydrogen bonding, hydrophobic and van der Waals interactions to cause polymer precipitation at a pH near 6.3 to 6.4.

Chitosan is recognized as a biodegradable, biocompatible, antibacterial and haemostatic biopolymer that is able to promote wound healing, drug absorption, and tissue reconstruction. Due to the aforementioned intrinsic properties, chitosan also has been widely explored in numerous cosmetic and pharmaceutical applications. Therefore, considering the great potential of chitosan, there is a continuous need to improve the properties of known chitosan formulations which are still considered as very promising for a wider range of biomedical applications.

It is disclosed herein a new methodology to rapidly form three-dimensional (3D) chitosan sponges in situ upon mixing of two injectable solutions using GDP (Guanosine 5'-Diphosphate) as the novel anionic crosslinker for chitosan. The ionic attractions between the phosphate and amine groups occur very rapidly upon mixing and form an intact chitosan sponge at a 5 to 6 pH range. The potential in situ application would involve injecting chitosan (pH 5-6) and GDP solutions simultaneously, which would result in the rapid formation of an intact chitosan sponge at the desired site. The 3D chitosan sponge could act as a scaffold for a multitude of tissue regeneration applications such as neural, cardiac, cartilage and bone regeneration. Chitosan porous scaffolds described herein can serve as an ECM analog to support cell attachment, proliferation, differentiation, and delivery of bioactive molecules.

In addition, it could act as a drug delivery system or vector to provide local controlled drug release, such as delivering anti-cancer drugs locally at the tumor site.

Chitosan can be directly used to physically entrap or chemically conjugate drugs or compounds in porous scaffolds as described herein. Chitosan has been used to deliver pharmacologically active compounds through different administrational routes including intranasal, oral, intra-peritoneal, and intramuscular routes. Chitosan/Insulin was administered through intranasal routes in rat and sheep (Ilium, 1996, Danbiosyst UK Limited, United States, vol. 5554388; 1998, Danbiosyst UK Limited, United States, vol. 5744166).

Chitosan has also been used to deliver nucleic acids varying from plasmid DNA to siRNA in vitro and in vivo as well. More than 40 examples of in vivo studies using siRNA have been reported (de Fougerolles et al., 2007, Nat Rev Drug Discov, 6:443-453) with delivery to ocular (Nakamura et al., 2004, Mol Vis, 10:703-711) and pulmonary targets (Howard et al., 2006, Mol Ther, 14:476-484), to the nervous system (Kumar et al., 2006, Plos Medicine, 3:505-514), liver (Soutschek et al., 2004, Nature, 432:173-178), tumors (Grzelinski et al., 2006, Hum Gen Ther, 17:751-766) and other organs by local or systemic delivery. In one example, chitosan/siRNA nanoparticles mediated TNF-α knockdown in peritoneal macrophages for anti-inflammatory treatment in an arthritis murine model (Howard et al., 2006, Mol Ther, 14:476-484). Several studies have examined the ability of chitosan to deliver siRNA in vitro and in vivo (Katas et al., 2006, J Control Release, 115:216-225).

Four preparations of GDP-crosslinked chitosan sponges were investigated. Two concentrations of chitosan (3 mg/ml and 6 mg/ml) solutions were prepared and were adjusted to a pH of 5 and 6 using a 1M sodium bicarbonate solution (Zhong et al., 2011, Gene Ther, 18: 232). The four groups were thus assigned the acronyms: C3PH5, C3PH6, C6PH5 and C6PH6 (FIGS. 1A, B, C, D, and G). It is important to mention that adding GDP to chitosan solutions at pH 7 yielded sponges with no mechanical integrity. Therefore, for in situ studies, the optimized pH range of chitosan solutions was 5 to 6.

Scanning Electron Microscopy (SEM) images of GDP-crosslinked chitosan sponges revealed a three-dimensional structure with heterogeneous pore sizes and excellent pore interconnectivity. The tested chitosan sponges were dehydrated to ethanol, and to amyl acetate. Critical point drying (CPD) was performed using a Leica EM CPD030 critical point dryer. The sponges were then coated with Gold/Palladium and imaged using a Hitachi S-4700 FE-SEM at 2 KeV and a current of 10 µA.

The sponges were formed of densely packed nanometer-sized polymer aggregates with an average aggregate size of 140±19 nm. The microstructure of the different sponge preparations did not present any apparent differences among themselves (FIGS. 1A, B, C, and D) but appeared significantly different from other sponges reported in the literature that were fabricated using freeze drying (Arponmaeklong et al., 2007, Int J Oral Max Surg, 36: 328; Griffon et al., 2006, Acta Biomaterialia, 2: 313). However, GDP-crosslinked chitosan sponges have a very similar structure to that reported for NeuroGel™ (Woerly et al., 2001, Biomaterials, 22: 1095). This physical resemblance is an indication that GDP-crosslinked chitosan sponges could be potential scaffolds for neural regeneration, since chitosan was shown to be a promising candidate for neural tissue regeneration (Kim et al., 2011, Journal of Biomedical Materials Research Part A, 97A: 395).

GDP-crosslinked chitosan sponges were found to retain water up to 10 times their own weight (see FIG. 1E). Chitosan sponges were placed in PBS overnight at 37° C. Excessive surface water was removed by a paper towel upon removal. $W_{wet}$ was then measured. Sponges were dried at 60° C. overnight, and the $W_{dry}$ was measured. The following equation was then used to calculate the percent water retention of the sponges:

$$\frac{W_{wet} - W_{dry}}{W_{dry}} \times 100 \tag{1}$$

The lower chitosan concentration (3 mg/ml) yielded more water retention, which was attributed to the ability of water to infiltrate the sponges and cause more swelling. C3PH5 had the highest water retention (1037%±43) and was significantly higher than C6PH5 (679%±44) and C6PH6 (784%±57) ($P<0.05$). However there were no statistical differences between C3PH5 and C3PH6 (938%±46). Also there were no significant differences between C6PH5 and C6PH6. In addition, the pH difference did not affect water retention within the two concentrations.

The impedance analyzer was used to calculate the gelation time after mixing the chitosan and GDP solutions. All sponges formed in less than 1.6 seconds (FIG. 1F). The time of sponge formation was measured using an Agilent 4294A high precision impedance analyzer. A constant frequency of 300 KHz and a source voltage of 300 mV were applied. GPIB computer data logging produced 400 data points, collected over a span of 20 seconds. The impedance of a fixed volume of chitosan (150 µl) solution was measured for 1 minute until the signal was stabilized. An equal volume of GDP (150 µl) solution was then introduced and the change of impedance was recorded. The time of sponge formation was calculated by measuring the time between GDP injection and the re-stabilization of the impedance. Measurements were done in triplicates for statistical analysis. As a control the signal produced by 150 µl of chitosan solution was recorded and another 150 µl was then added, and there was no change in the impedance observed. Therefore, it was concluded that the decrease in impedance observed with crosslinking was due to GDP crosslinking and not to volume increase.

C6PH5 had the fastest gelation time (1.06±0.0384 seconds) and was significantly lower than all other sponges ($P<0.05$). While C6PH6 was the slowest forming sponge (1.58±0.00667 seconds) and was significantly slower than C3PH6 and C6PH5 ($P<0.05$), but was not significantly different from C3PH5. There was no significant difference between C3PH5 (1.48±0.0570) and C3PH6 (1.38±0.0153). However, there were significant differences between chitosan sponges within similar pH groups. An interesting correlation was observed between the water retention data and the time of sponge formation. At a chitosan concentration of 3 mg/ml, the time of sponge formation was found to be proportional to water retention. A longer time of formation resulted in the retention of more water within the sponge. At 6 mg/ml, a similar correlation could be observed, although there was no significant difference in water retention between C6PH5 and C6PH6.

FTIR analysis of the GDP-crosslinked chitosan was performed to assess the incorporation of GDP within the polymeric structure of chitosan (FIG. 1H). For example, C6PH5 was washed thoroughly in distilled water and dried at 60° C. overnight prior to FTIR analysis. Infrared measurements were performed using a Perkin Elmer FTIR spectrometer with an ATR attachment (Pike Technologies). The spectra were collected in absorption mode, using 64 scans, and a resolution of 4 cm$^{-1}$.

The spectrum of GDP-crosslinked chitosan sponges showed peaks from GDP (777 cm$^{-1}$, 905 cm$^{-1}$, 1178 cm$^{-1}$, 1229 cm$^{-1}$, and 1533 cm$^{-1}$) incorporated with the chitosan peaks, and thus confirms the crosslinking of chitosan using GDP. Finally, X-ray Diffraction (XRD) patterns and the crystallinity index ($C_r I_{100}$) revealed a decrease in crystallinity and an increase in the amorphous phase in the GDP-crosslinked chitosan as compared to dry chitosan powder (FIG. 1I). A Bruker D8 Discovery X-Ray Diffractometer was used to study the crystallinity of chitosan and the four preparations using: a 2θ range from 2 to 60°, a rate of 4°/min, 40 kV and 80 mA. The Crystallinity index ($C_r I_{100}$) was calculated using the following equation (Ren et al., 2005, Carbohyd Res, 340: 2403; Focher et al., 1990, Carbohyd Polym, 12: 405):

$$C_r I_{100} = \left( \frac{I_{110} - I_{am}}{I_{110}} \times 100 \right) \quad (2)$$

$I_{110}$ is the lattice diffraction measured at 2θ=20 and $I_{am}$ is the amorphous region diffraction measured at 2θ=16.

The crystallinity of the as-purchased chitosan powder was similar to previous reports (Ren et al., 2005, Carbohyd Res, 340: 2403), and interestingly the trend of the four sponges followed those of the water retention and gelation time. C6PH5, having the fastest gelation rate, rapidly fixed chitosan chains in certain conformations that inhibited the slower formation of ordered crystalline structures due to diffusion.

Mechanical indentation using a stainless a steel ball (Ø=1 mm) was used to measure the modulus of Elasticity (E) of the chitosan sponges (see FIGS. 2A, B). The findings were consistent with water retention and gelation times results (FIGS. 1E, F). Indentation using a Ø=1 mm stainless steel sphere was used to measure the mechanical properties of the chitosan sponges. The setup included a Fullam miniature loading stage in conjunction with a FUTEK 20 g load cell. The rate of deformation of 50 μm/s was used and the force was measured until a threshold of 0.15 N. All measurements were repeated in triplicates for statistical analysis.

$$F = \frac{4}{3} \left( \frac{E}{(1-v)^2} \right) \delta^{\frac{3}{2}} R^{\frac{1}{2}} \quad (3)$$

A model (Eq. 3) assuming an elastic half space and a rigid spherical indenter was used to calculate the modulus of elasticity (E) from the force-displacement graphs (McKee et al., 2011, Tissue Eng Part B Rev, 17: 155). F is the force, v is Poisson's ratio, δ is the indentation displacement, and R is the radius of the spherical indenter. Eq. 2 was fitted to the experimental data with a chi-square tolerance of 10$^{-9}$ and assuming a Poisson's ratio of 0.5 since the sponge was fully swollen and was assumed to act as a rubber-like material (Kloxin et al., 2010, Adv Mater, 22: 3484; Zhu et al., 2011, J Biomech, 44: 2356).

C6PH5 found to have the shortest gelation time and least water retention was significantly more rigid (E=0.33±0.039 MPa) than the other three sponge groups (P<0.05). The increased protonation of amine groups at pH 5 and the high chitosan concentration, increased sites available for crosslinking and thus resulted in a more rigid C6PH5 sponge. There were no significant differences between C3PH5 (E=0.12±0.0087 MPa), C3PH6 (E=0.11±0.010 MPa) and C6PH6 (E=0.13±0.016 MPa). The moduli of elasticity of the sponges revealed a soft biomaterial that could be used for tissue regeneration of soft human tissues such as articular cartilage (Schinagl et al., 1997, J Otrhop Res, 15: 499), spinal cord (Bilston et al., 1996, Ann Biomed Eng, 24: 67), brain (Miller et al., 2000, J Biomech, 33: 1369) and heart muscle (Zhu et al., 2011, J Biomech, 44: 2356).

In order to investigate the cell compatibility of the sponges, 3T3 fibroblasts were cultured on the sponges for 3 days. Fibroblasts were cultured on the four sponge preparations for 3 days using DMEM supplemented with 10% Calf Bovine Serum (CBS) and 1% PenStrep. Sponges containing cells were then washed with sterile PBS and fixed for 30 minutes in 4% paraformaldehyde. Sponges were then dehydrated to ethanol and then to amyl acetate. CPD was then carried out to dry the sponges containing cells. The sponges were coated with Gold/Palladium and imaged using a Hitachi S-4700 FE-SEM at 2 KeV and a current of 10 μA.

Figure 2:
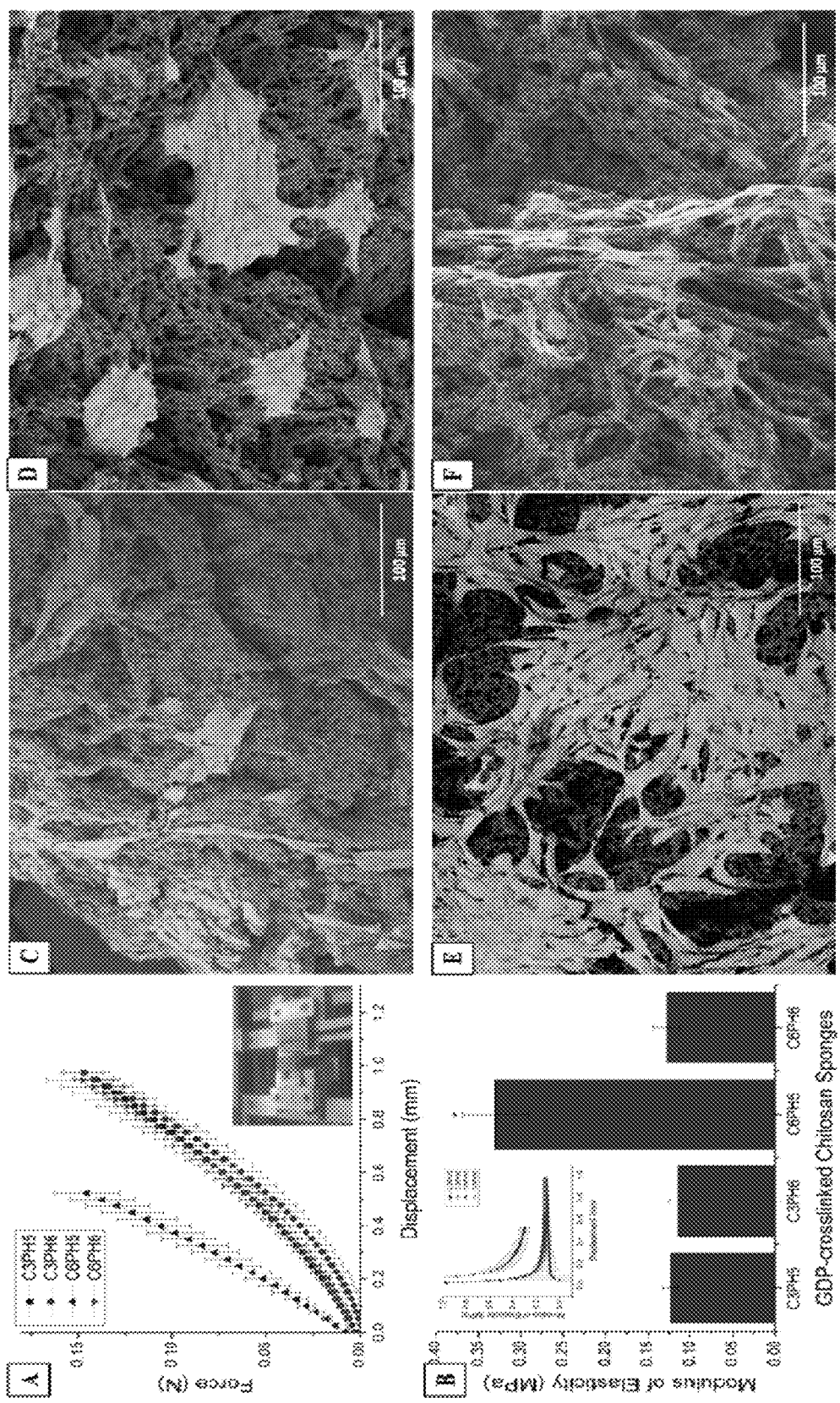
FIG. 2A illustrates the force-displacement graph of the four sponges described herein.
FIG. 2B shows the moduli of elasticity of the sponges.
FIGS. 2C, 2D, 2E and 2F are SEM images of 3T3 fibroblasts cultured on C3PH5, C3PH6, C6PH5 and C6PH6 respectively.

SEM images revealed fibroblast attachment and spreading on the surface of the sponges (see FIGS. 2 C, D, E and F). This is a preliminary indication of the cell/tissue compatibility of the sponges.

Figure 3:
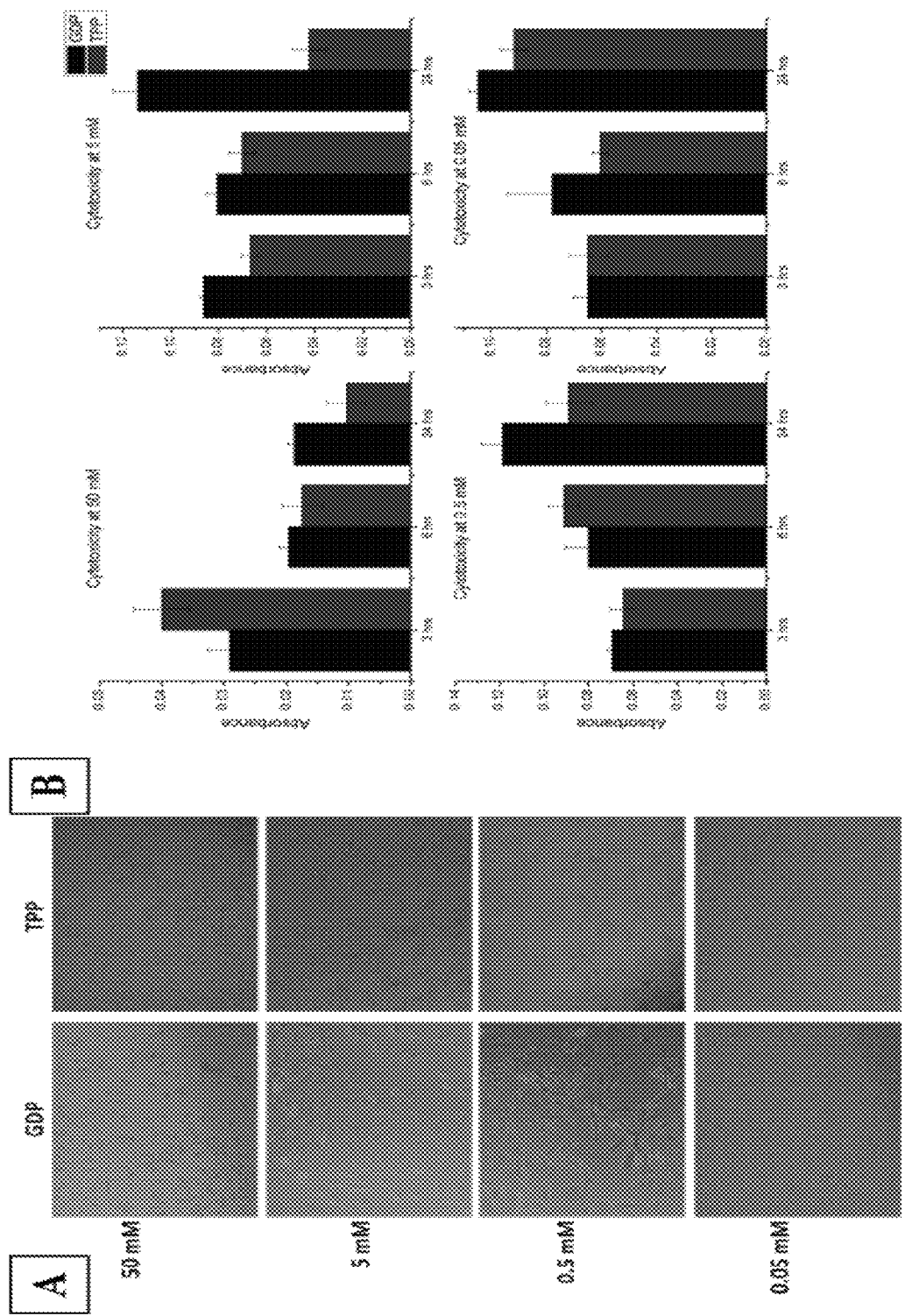
FIG. 3 illustrates the comparison of the cytotoxicity of GDP and TPP at different concentrations.

Crosslinking of chitosan using GDP occurs due to the electrostatic attractions between the anionic phosphate groups of GDP and the cationic amine groups of chitosan. Another anionic crosslinker used in the art is tripolyphosphate (TPP), which has been widely used to fabricate chitosan nanoparticles, microparticles and fibers (Pati et al., 2011, Carbohyd Res, 346: 2582). The cytotoxicity of GDP was compared to tripolyphosphate (TPP) at concentrations from 0.05 mM to 50 mM using 3T3 fibroblasts. GDP is significantly less cytotoxic to fibroblasts at concentrations higher than 5 mM after 24 hours of culture (FIG. 3). The cytotoxicity of TPP at concentrations higher than 5 mM has also been demonstrated in a recent study (Pati et al., 2012, Journal of Materials Science-Materials in Medicine, 23: 1085).

It was observed in confocal images that MC-3T3 cells adhered and sent out processes after day 3 in culture. However, at day 14 the cells assumed a more round morphology which was more compact and resembling a mature osteoblast. MC-3T3 cultured on TCP spread out at Day 3 and were confluent by Day 14. (see FIG. 4A).

The ALP activity, which is a measure of MC-3T3 osteogenesis and of bone mineralization, was almost 100 fold higher in the chitosan sponges as compared to the TCP (see FIG. 4B). However, there was no significant increase between day 7 and day 14 in the sponge groups, while there was a significant increase in the TCP control groups (4 fold increase).

Confocal images were acquired of OPCs cultured on the four sponge formulations (washed and unwashed) for 5 days (FIG. 5A). The OPCs were stained for the progenitor marker A2B5, the more mature pre-oligodendrocyte marker GalC and the nuclei. The images demonstrate the ability of OPCs to attach to the chitosan sponges and that A2B5$^+$ OPCs had a bipolar morphology, which is similar to in vivo morphology. Also, GalC$^+$ cells sent out processes into the sponge and had a similar morphology as in vivo.

It can be seen from Box and Whiskers plots that most sponges (Washed: C3PH5, C6PH5 and C6PH6; Unwashed: all sponges) promoted more differentiation than the controls even in the presence of PDGF and bFGF that are supposed to suppress differentiation (FIG. 5B). These results support the prediction that the guanosine in the GDP can induce OPC differentiation.

A 3D rendering of OPCs cultured on washed and unwashed sponges demonstrated the slight infiltration of the OPCs in the sponges (FIG. 5C).

It is thus described herein a novel methodology to rapidly form chitosan sponges using GDP as an anionic crosslinker. The proposed injectable system possesses excellent physical and chemical properties that make it an excellent candidate compared to currently available injectable hydrogels. The rapid gelation upon mixing of the chitosan and GDP solutions (t<1.6 sec), the formation of a porous structure with interconnected pores, the ability to retain water up to 10 times its weight, the mechanical properties resembling those of human soft tissue and finally good cell compatibility make GDP-crosslinked chitosan sponges excellent injectable scaffolds.

The present disclosure will be more readily understood by referring to the following.

EXAMPLE I

GDP-crosslinked Chitosan Sponges Fabrication

High Molecular Weight Chitosan (Degree of Deacetylation>90%; 3000 cp viscosity) was purchased from MP Biomedicals, LLC (CAT No. 150597). GDP was purchased from Sigma Aldrich (CAT No. G7127). Hydrochloric Acid (50% v/v) was purchased from LabChem Inc (CAT No. LC15130-3).

Two concentrations of chitosan (3 mg/ml and 6 mg/ml) solutions were prepared by dissolving 30 and 60 mg of chitosan in 10 ml of 0.01M HCl respectively. The pH was increased to 5 and 6 by adding 0.2 to 0.5 ml of 1M sodium bicarbonate solution (Zhong et al., 2011, Gene Ther, 18: 232). The four groups were thus assigned the acronyms: C3PH5, C3PH6, C6PH5 and C6PH6. Sodium bicarbonate allows chitosan to remain dissolved in solution up to a pH of 7. GDP (30 mg) was dissolved in 0.3 ml of distilled water to acquire a final GDP concentration of 15 mg/ml. The chitosan (1.7 ml) and GDP (0.3 ml) solutions were placed in a 37° C. incubator for 15 minutes. The GDP solution was then added to the chitosan solution at once and not drop-wise. A GDP-crosslinked chitosan sponge formed instantaneously and thickened as time progressed. The sponge was removed and washed thoroughly in PBS until further characterization.

EXAMPLE II

Figure 4:
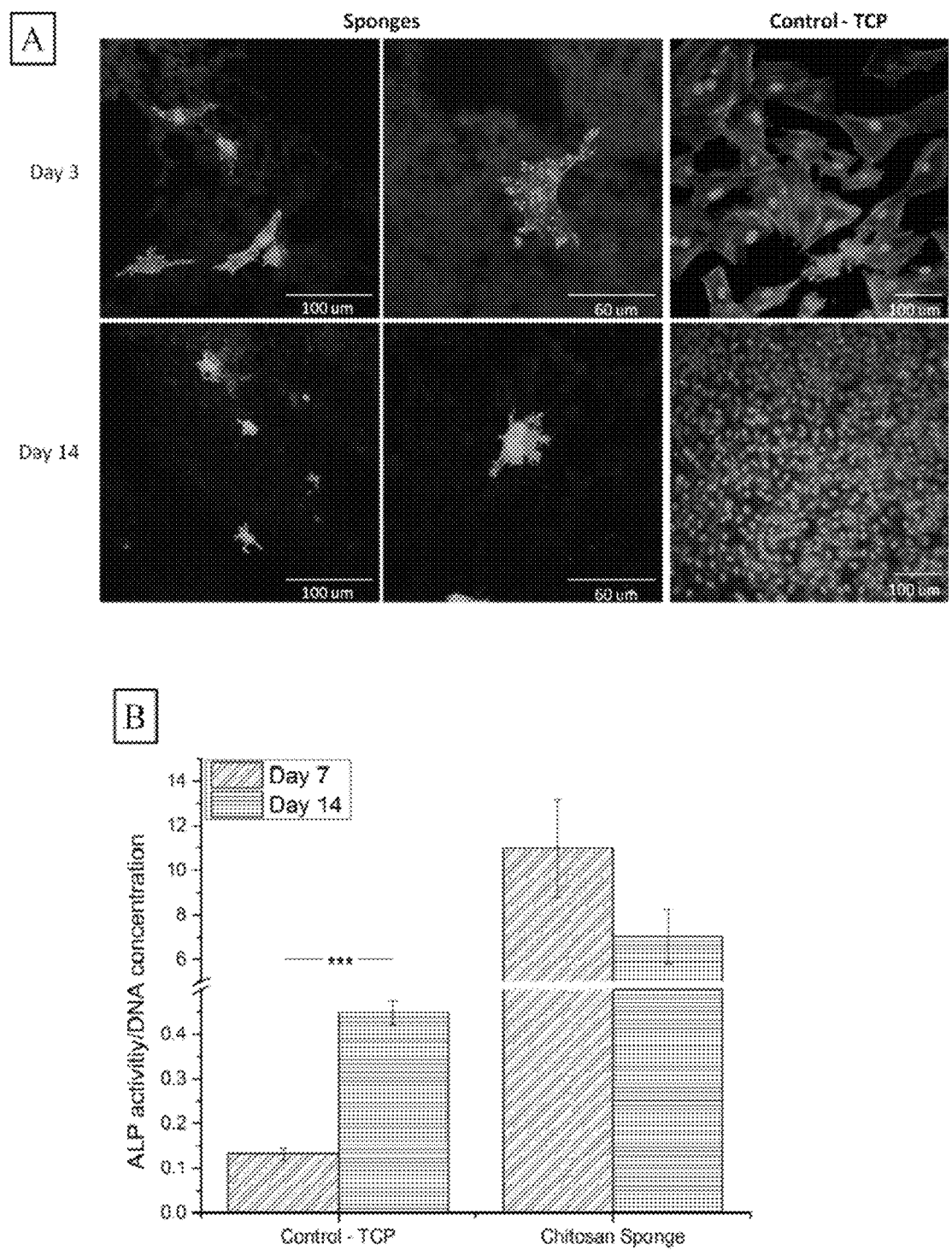
FIG. 4A represents confocal images demonstrating MC-3T3 morphology after culturing on chitosan sponges and tissue culture plates (TCP) after 3 and 14 days.
FIG. 4B illustrates an histogram showing measured ALP activity (*** $P<0.001$).

Chitosan Sponges Promotion of MC-3T3 Attachment and Differentiation in the Osteoblast Lineage MC-3T3 cells were cultured on the GDP-crosslinked chitosan sponges (C6PH6) at a concentration of $1 \times 10^4$ cells/well. Cells were cultured for up to 14 days and the media was changed once at day 7. The media used was α-MEM supplemented with 10% FBS and 1% PenStrep. No ascorbic acid or β-glycerophosphate was added to the culture media. Cell attachment and Alkaline Phosphatase (ALP) activity were assessed using confocal microscopy, and an ALP colorimetric assay kit respectively. Confocal images were acquired after 3 and 14 days of culture, and ALP was done after 7 and 14 days of culture. For confocal imaging, sponges with adherent cells were washed three times using PBS and fixed using Paraformaldehyde for 30 minutes. The sponges were then washed with PBS, phalloidin-Alexa488 was used to stain actin, and nuclei were stained using Hoechst. Samples were then mounted and imaged. As for ALP activity, the sponges were thoroughly washed with PBS and then homogenized in lysis buffer for 30 minutes. The sponge and cellular debris were removed through centrifuged at 13,000 g for 3 minutes. 5 mM pNPP solution was then added to the supernatant and incubated for 1 hour at room temperature in the dark. A stop solution was then added to stop the reaction. Controls were prepared by culturing MC-3T3 in a 6-well tissue culture plates. ALP activity was normalized to DNA content measured using picogreen assay (FIG. 4)

EXAMPLE III

Figure 5:
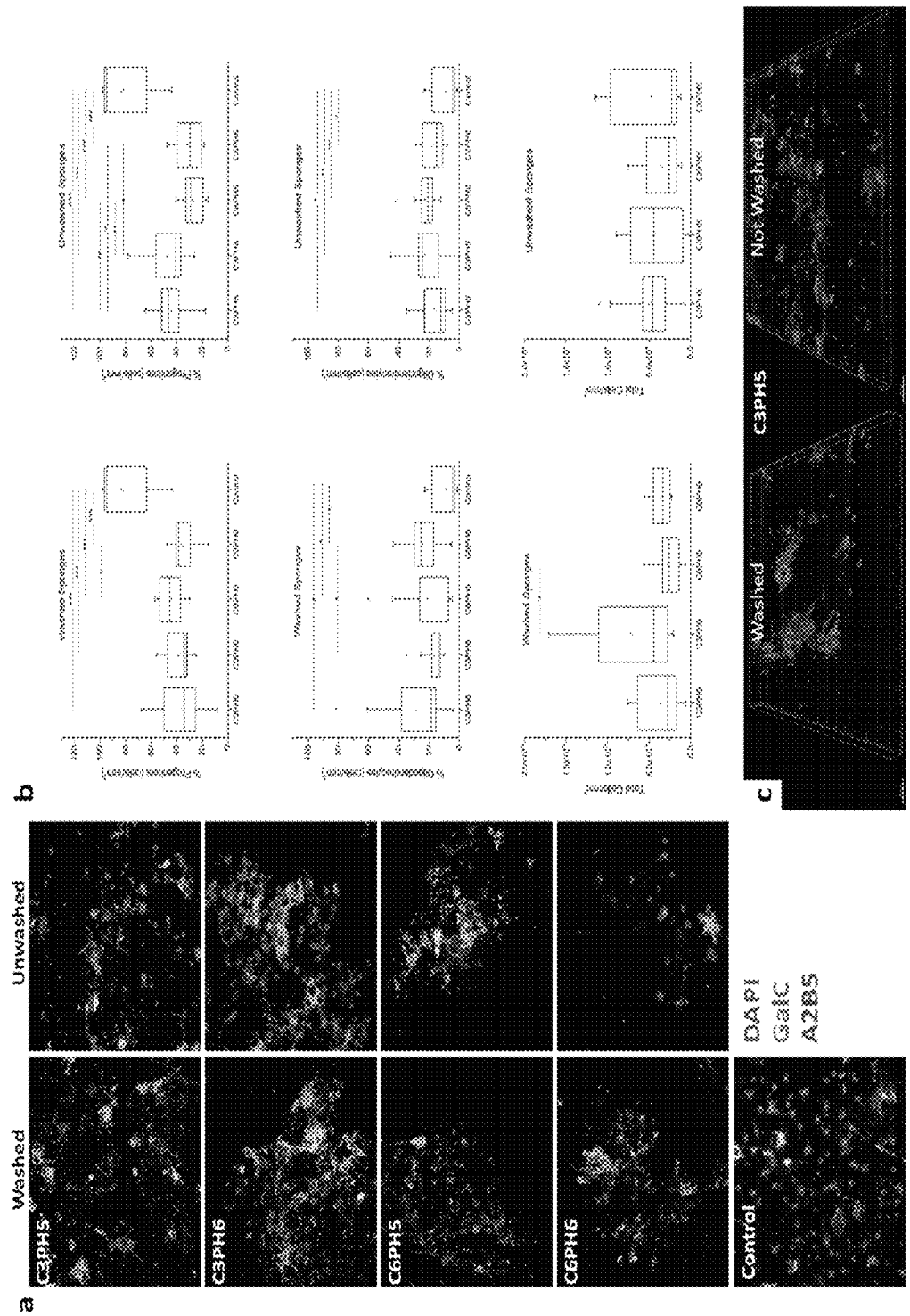
FIG. 5A represents confocal images of OPCs cultured on the four sponge formulations (washed and unwashed) for 5 days.
FIG. 5B illustrates Box and Whiskers plots demonstrating the percent progenitors, percent oligodendrocytes and total cell density (cells/mm$^3$) in both washed and unwashed sponges (n=3 independent experiments with triplicates in each, *$P<0.05$,  $P<0.01$, * $P<0.001$)
FIG. 5C illustrates a 3D rendering of OPCs cultured on washed and unwashed sponges demonstrating the slight infiltration of the OPCs in the sponges.

Chitosan Sponges Promote Oligodendrocyte Progenitor Cells (OPCs) Attachment and Differentiation OPCs were cultured on the four sponge formulations (washed and unwashed) at a concentration of $5 \times 10^4$ cells/well. After the first day of culture, the media was changed to Serum Free Media (SFM) supplemented with PDGF and bFGF in order to suppress differentiation. The cells were then left to grow on the sponges and the controls (Poly-ornithine-coated cover slips) for 4 days. The cells were then stained with A2B5 (a progenitor marker), GalC (a more mature pre-oligodendrocyte marker), and Nuclei. These experiments were repeated three independent times with n=3 in each experiment (total n=9). Cell count was performed per imaged volume to get the cell density (cells/mm$^3$) (FIG. 5).

While the invention has been described in connection with specific embodiments thereof, it will be understood that it is capable of further modifications and this application is intended to cover any variations, uses, or adaptations of the invention as within known or customary practice within the art to which the invention pertains, and as follows in the scope of the appended claims.

What is claimed is:

1. A gelling composition comprising:
    a) chitosan; and
    b) Guanosine 5'-Diphosphate (GDP),
    wherein the composition forms a gel when the chitosan is mixed with the GDP at a pH range from 5 to 6.

2. The gelling composition of claim 1, wherein the composition gels in 1 to 5 seconds.

3. The composition of claim 2, wherein the composition gels in 1.6 seconds.

4. The composition of claim 1, further comprising sodium bicarbonate.

5. The composition of claim 4, comprising 1M of sodium bicarbonate.

6. The composition of claim 1, comprising chitosan at a concentration of 3 mg/ml to 6 mg/ml.

7. The composition of claim 1, wherein the chitosan has a degree of deacetylation of more than 85%.

8. The composition of claim 1, wherein the chitosan has a degree of deacetylation of more than 90%.

9. A method of manufacturing the gelling composition of claim 1 comprising:
    a) dissolving chitosan in an acidic medium;
    b) increasing the pH of chitosan between 5 and 6; and
    c) adding a solution containing Guanosine 5'-Diphosphate (GDP) forming a gel.

10. The method of claim 9, wherein the acidic medium is HCl.

11. The method of claim 9, wherein the pH of chitosan is increased by adding a sodium bicarbonate solution.

12. The method of claim 9, wherein the GDP solution and the chitosan solution are maintained at 37° C. separately before the solution of GDP is added to the chitosan solution.

\* \* \* \* \*